(12) United States Patent
Bergin et al.

(10) Patent No.: US 7,892,290 B2
(45) Date of Patent: *Feb. 22, 2011

(54) FLUTED SLEEVE HIP PROSTHESIS FOR MODULAR STEM

(75) Inventors: Alisha W. Bergin, Southaven, MS (US); Jerry L. Jones, Memphis, TN (US); David C. Kelman, Collierville, TN (US); Richard D. Lambert, Germantown, TN (US); Terry W. McLean, Cordova, TN (US)

(73) Assignee: Smith & Nephew, Inc. (GB)

( * ) Notice: Subject to any disclaimer, the term of this patent is extended or adjusted under 35 U.S.C. 154(b) by 968 days.

This patent is subject to a terminal disclaimer.

(21) Appl. No.: 11/625,151

(22) Filed: Jan. 19, 2007

(65) Prior Publication Data

US 2007/0118229 A1  May 24, 2007

Related U.S. Application Data (63) Continuation-in-part of application No. 11/139,926, filed on May 27, 2005, now Pat. No. 7,575,603.

(60) Provisional application No. 60/575,636, filed on May 28, 2004, provisional application No. 60/655,129, filed on Feb. 22, 2005, provisional application No. 60/761,056, filed on Jan. 20, 2006.

(51) Int. Cl.
*A61F 2/36* (2006.01)
(52) U.S. Cl. ............... 623/23.46; 623/23.22; 623/23.31
(58) Field of Classification Search ... 623/23.15–23.38, 623/19.14, 23.44–23.46
See application file for complete search history.

(56) References Cited

U.S. PATENT DOCUMENTS

| 3,067,740 | A |   | 12/1962 | Hoboush |
| 3,943,576 | A |   | 3/1976 | Sivash |
| 4,516,277 | A |   | 5/1985 | Butel |
| 4,549,319 | A | * | 10/1985 | Meyer ..................... 623/23.23 |
| 4,661,112 | A |   | 4/1987 | Muller |

(Continued)

FOREIGN PATENT DOCUMENTS

DE   19725773   12/1998

(Continued)

OTHER PUBLICATIONS

Atlas of Hip Arthroplasty; US Femoral Implants 1938-2008 by George Branovacki, M.D. Various excerpts of catalogs for hip stems, 12 pages (2008).

(Continued)

*Primary Examiner*—David H Willse
*Assistant Examiner*—Megan Wolf
(74) *Attorney, Agent, or Firm*—David A. Warmbold; David A. Chambers (57) ABSTRACT

An intramedullary implant for mounting within an intramedullary canal of a bone is disclosed. The intramedullary implant includes a lower stem portion, an upper stem portion, and a modular sleeve body. The modular sleeve body is connected to one of the lower stem portion or the upper stem portion. The sleeve body includes an inner portion that covers at least a segment of the upper stem portion and has one or more longitudinally extending bone engagement members for engagement with the bone.

37 Claims, 9 Drawing Sheets

U.S. PATENT DOCUMENTS

| | | | |
|---|---|---|---|
| 4,756,711 A | | 7/1988 | Mai et al. |
| 4,790,852 A | | 12/1988 | Noiles |
| 4,808,186 A | | 2/1989 | Smith |
| 4,846,839 A | | 7/1989 | Noiles |
| 4,944,759 A | * | 7/1990 | Mallory et al. ........... 623/22.31 |
| 4,944,761 A | | 7/1990 | Stuhmer et al. |
| 4,986,834 A | | 1/1991 | Smith et al. |
| 5,030,238 A | | 7/1991 | Nieder et al. |
| 5,100,407 A | | 3/1992 | Conrad et al. |
| 5,171,323 A | | 12/1992 | Willert et al. |
| 5,336,265 A | | 8/1994 | Serbousek et al. |
| 5,507,829 A | | 4/1996 | Thongpreda et al. |
| 5,509,935 A | | 4/1996 | Fosco et al. |
| 5,549,702 A | | 8/1996 | Ries et al. |
| 5,571,193 A | | 11/1996 | Kampner |
| 5,593,446 A | | 1/1997 | Kuoni |
| 5,702,482 A | | 12/1997 | Thongpreda et al. |
| 5,755,805 A | | 5/1998 | Whiteside |
| 5,776,204 A | | 7/1998 | Noble et al. |
| 5,902,340 A | * | 5/1999 | White et al. ................ 128/898 |
| 5,935,172 A | | 8/1999 | Ochoa |
| 6,139,584 A | | 10/2000 | Ochoa et al. |
| 6,200,350 B1 | | 3/2001 | Masini |
| 6,264,699 B1 | | 7/2001 | Noiles et al. |
| 6,383,225 B2 | | 5/2002 | Masini |
| 6,527,807 B1 | | 3/2003 | O'Neil et al. |
| 6,554,865 B2 | | 4/2003 | Grusin et al. |
| 6,740,120 B1 | | 5/2004 | Grimes |
| 6,981,991 B2 | | 1/2006 | Ferree |
| 7,575,603 B2 | | 8/2009 | Bergin et al. |
| 2002/0120344 A1 | | 8/2002 | Meulink et al. |
| 2002/0143402 A1 | | 10/2002 | Steinberg |
| 2004/0002759 A1 | | 1/2004 | Ferree |
| 2004/0006392 A1 | | 1/2004 | Grusin et al. |
| 2004/0122437 A1 | | 6/2004 | Dwyer et al. |
| 2005/0143837 A1 | | 6/2005 | Ferree |
| 2006/0004465 A1 | | 1/2006 | Bergin et al. |
| 2006/0241776 A1 | * | 10/2006 | Brown et al. ............. 623/20.16 |
| 2009/0270860 A1 | | 10/2009 | Bergin et al. |

FOREIGN PATENT DOCUMENTS

| | | |
|---|---|---|
| EP | 145938 | 6/1985 |
| EP | 0159462 | 10/1985 |
| EP | 0623321 | 11/1994 |
| EP | 0709071 A2 | 5/1995 |
| EP | 0668064 | 8/1995 |
| EP | 0 815 809 B1 | 1/1998 |
| EP | 1698304 | 9/2006 |
| FR | 2483218 | 12/1981 |
| FR | 2643256 | 8/1990 |
| WO | WO8302555 | 8/1983 |
| WO | WO0002504 | 1/2000 |

OTHER PUBLICATIONS

Office Action dated Dec. 8, 2009 in U.S. Appl. No. 11/625,151.
Response dated May 7, 2010 in U.S. Appl. No. 11/625,151.
Office Action dated Sep. 6, 2007 in U.S. Appl. No. 11/139,926.
Response dated Mar. 6, 2008 in U.S. Appl. No. 11/139,926.
Supplement Amendment and Response dated Apr. 22, 2008 in U.S. Appl. No. 11/139,926.
Office Action dated Dec. 30, 2008 in U.S. Appl. No. 11/139,926.
Response dated Feb. 5, 2009 in U.S. Appl. No. 11/139,926.
Notice of Allowance dated Apr. 2, 2009 in U.S. Appl. No. 11/139,926.

* cited by examiner

FLUTED SLEEVE HIP PROSTHESIS FOR MODULAR STEM

CROSS-REFERENCE TO RELATED APPLICATIONS

This application is a continuation-in-part of U.S. patent application Ser. No. 11/139,926 filed on May 27, 2005, now U.S. Pat. No. 7,575,603 which claimed priority to U.S. Provisional Patent Application No. 60/575,636 filed on May 28, 2004 and U.S. Provisional Patent Application No. 60/655,129 filed on Feb. 22, 2005. This application claims the benefit of U.S. Provisional Application No. 60/761,056 filed Jan. 20, 2006. The disclosure of each prior application is incorporated by reference in its entirety.

BACKGROUND OF THE INVENTION

1. Field of the Invention

The present invention relates, in general, to intramedullary implants and stems, and particularly hip stems, that are provided to replace worn joints.

2. Related Art

Artificial implants, including hip joints, shoulder joints, and knee joints, are widely used in orthopedic surgery. Artificial hip and shoulder joints are generally ball and socket joints, designed to match as closely as possible the function of the natural joint. To duplicate a joint's natural action, a total joint replacement implant has three parts: the stem, which fits into the femur or humerus and provides stability; the ball, which replaces the spherical head of the femur or humerus; and the cup, which replaces the worn-out hip or shoulder socket.

There are many types of stems that may be used in joint replacement surgery to secure the artificial ball that will articulate with the artificial socket. Some stems are modular, allowing a greater range of options during the surgery. Each part comes in various sizes in order to accommodate various body sizes and types. In some designs, the stem and ball are one piece; in other designs, they may be provided as separate pieces. In further designs, the stem and ball may feature a modular body, a removable neck, or any combination of these or additional features. Such designs and their combinations will be referred to throughout this document as "modular," and are intended to allow for additional customization and fit.

Specifically, modular stems may be provided in any number of lengths and widths. Corresponding modular bodies and heads may be provided in various sizes, allowing the surgeon to select the best options for the particular patient. Other stems may be non-modular, and may provide a stem, neck, and ball in a one-piece configuration.

In choosing a proper implant, the surgeon will consider individual patient needs. One consideration may be modularity; another consideration may be stability needed based on proximal bone degeneration that may have already taken place. If there is substantial bone degeneration, the surgeon will likely choose a stem with additional distal fixation features to prevent any more proximal bone erosion. In other words, the surgeon must seek supportive bone more distally, rather than relying on support from the proximal bone. This is particularly an issue in revision surgeries, although it may also be a concern during a primary surgery. Accordingly, there is a challenge to provide stems that are stable and provide efficient loading for distribution and implant longevity, but that also allow the surgeon as may options as possible.

The two current, but different, distal femoral fixation philosophies include relying on (a) a cylindrical coated stem (the coating may be a biological coating or a bead coating, described more fully below) or (b) a tapered grit-blasted stem. Both types of stems have disadvantages.

Some surgeons using traditional, conical, tapered hip stems find it difficult to recreate the femoral neck height because the stem locks into place within the femoral canal too high or too low. The primary factors resulting in stem placement uncertainty are the difficulty in reproducible reamer depth placement and variations in bone quality. Some revision tapered hip stems offer modular necks of various heights to compensate for the difficulty, but offering modular necks as the sole solution may increase the complexity of the surgical procedure.

Cylindrical biologically and/or bead coated revision hip stems have the advantage of a more reproducible fit during the surgery. However, the biological enhancement coating in conjunction with the cylindrical shape of the implant may cause stress-shielding to the proximal bone due to the concentration of loading forces in the mid to distal portion of the stem. Unlike a tapered stem, a cylindrical stem loads the bone entirely against shear forces within the femoral canal. The inefficient loading distribution likely causes bone loss proximally, making future revision surgeries even more difficult.

Cylindrical stems are typically bowed stems. Recently, another design that has been explored is a tapered stem with a cylindrical bow at its distal end. When seeking support for the prosthesis more distally, a surgeon may alternatively use a longer revision stem. With long stems, the most distal section of the stem must be modified to accommodate the anterior bow of the femur. This is because, although a longer stem can provide additional stability, the length of the stem could perforate the cortex of the femur during insertion if the stem is not slightly curved to follow the natural curve of the femur. Current options for modifying the stem are bowing, angling, or otherwise shaping the distal section of the stem to follow the natural curve of the femur, or adding a chamfer slot in the stem. Accordingly, although bowed stems can provide increased stability, they can limit stem neck orientation options because the one-piece options do not always provide the modularity that may be desired at times due to the stem being limited to being orientated in the proper direction of the bow. If an independent body and/or neck portion is provided for use with the stem, orientation options may be increased, but as mentioned, this may also increase the complexity of the surgery.

Other stems designs seek to provide additional stability by offering bone in-growth or bone on-growth surfaces. These surfaces can be physically formed by roughening the stem surface, providing metallic beads, grit blasting, or forming a porous surface in the stem surface such that it supports bone growth. Additionally or alternatively, the surface of the implant may be provided with hydroxyapatite or any other biological substance that promotes bone in-growth or on-growth.

Other attempts to provide stems with greater stability have included providing grooves at certain areas on the shaft portion. The grooves are typically intended to vary the stiffness along the stem shaft to provide stiffness and stability in some areas but less stiffness in other areas.

Many times a patient undergoing a primary or revision hip arthroplasty will have anatomy such that the typical one piece hip prostheses can not adequately address the patient needs. A modular hip stem implant with the ability to independently size the metaphyseal and diaphyseal regions can offer the surgeon more options for the patient. However, many of the current modular prostheses require the surgeon to remove an excessive amount of bone and fill the void with the implant to obtain adequate stability. Many of the current systems require a complex surgical technique as well.

However, there is a need in the art to provide an intramedullary stem that provides strong distal fixation particularly for revision surgeries when there is not much bone at the proximal portion of the bone. There is also a need for a stem with the desired distal fixation, but that also provides flexible options that are not limited by stem length and the requirement of a bowed portion at the distal end of the stem. There is also a need for a stem that has axial and rotational stability, while also providing a certain amount of flex. There is also a need for a stem that provides increased surface area for bone in-growth and/or on-growth.

There is a need in the art for a modular hip system containing modular sleeves. There is a need in the art for modular prostheses that require only a minimum amount of bone removal. Finally, there is a need in the art to simplify surgical techniques to obtain stabile modular hip implants.

SUMMARY OF THE INVENTION

The invention is, briefly, an intramedullary implant for mounting within an intramedullary canal of a bone. The intramedullary implant includes a lower stem portion, an upper stem portion, and a modular sleeve body. The modular sleeve body is connected to one of the lower stem portion or the upper stem portion. The sleeve body includes an inner portion that covers at least a segment of the upper stem portion and has one or more longitudinally extending bone engagement members for engagement with the bone.

In some embodiments of the invention, the sleeve body has a proximal end portion, a distal end portion, and a middle portion therebetween, and the longitudinally extending bone engagement member is positioned on at least one of the proximal end portion, the distal end portion, or the middle portion.

In another embodiment of the invention, the modular sleeve body further includes a groove. The groove may be formed as part of a base portion. In yet another embodiment of the invention, a width of the groove is related to a width of the bone engagement member. In still another embodiment of the invention, there may be provided a groove located on each side of the bone engagement member. In some embodiments, the modular sleeve body further includes an auxiliary bone engagement member that engages the groove.

In another embodiment of the invention, the sleeve body includes an outer portion. The shape of the outer portion may be frusto-conical or cylindrical. In yet another embodiment of the invention, the outer portion has both a frusto-conical region and a cylindrical region.

In still another embodiment of the invention, the longitudinally extending bone engagement member may have a constant height relative to the outer portion. Alternatively, the longitudinally extending bone engagement member is tapered relative to the outer portion.

In some embodiments of the invention, the sleeve body includes a base portion. The base portion may be arcuate or tapered.

In one embodiment of the invention, the outer portion of the sleeve body and the bone engagement member are made from generally the same material. Alternatively, the outer portion of the sleeve body and the bone engagement member are made from generally different materials.

In some embodiments of the invention, the sleeve body includes a casing of a material that encapsulates the outer portion. In some embodiments, the casing is made of a bioabsorbable material.

In other embodiments of the invention, the outer portion includes a textured surface. The textured surface may be a sintered coating, chemically etched, or abrasively roughened.

The longitudinally extending bone engagement member provides for rotational and axial stability for the intramedullary implant. The longitudinally extending bone engagement member provides for a minimal amount of bone removal in comparison to the state of the art and significantly reduces the complexity of the surgical procedure.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The accompanying drawings, which are incorporated in and form a part of the specification, illustrate the embodiments of the present invention and together with the written description serve to explain the principles, characteristics, and features of the invention. In the drawings.

DETAILED DESCRIPTION OF THE EMBODIMENTS

The following description of the preferred embodiment(s) is merely exemplary in nature and is in no way intended to limit the invention, its application, or uses.

Intramedullary stems developed for enhanced distal stabilization are often formed as cylindrical stems, grit-blasted tapered stems, or long stems (which are often necessarily bowed due to their use and the patient's anatomy.) All of these stems have drawbacks. For example, most bowed stems limit the surgeon's ability to orient the stem; if it is not modular, the stem can only be implanted such that the bow corresponds to the natural curve of the patient's bone. Accordingly, the present invention provides an alternate to current stems, while still providing enhanced distal fixation, modularity options, enhanced stabilization, and flexibility.

Figure 1:
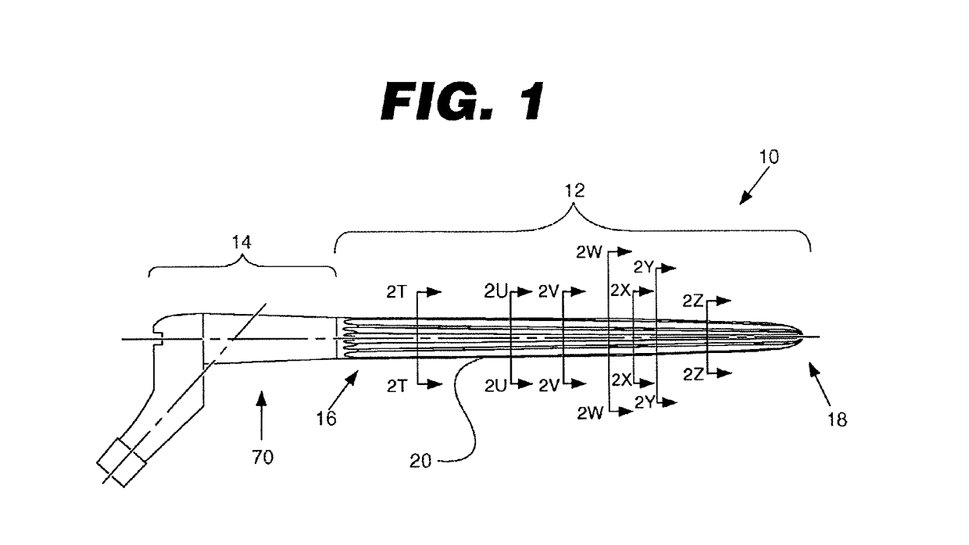
FIG. 1 is a side plan view of a stem.

As shown in FIG. 1, intramedullary implant 10 has a shaft 12 with a longitudinal length and an upper stem portion 14. The intramedullary implant 10 also may be referred to as a stem, and the shaft 12 also may be referred to as a lower stem portion. The upper stem portion 14 is adapted to receive a ball or head (not shown) to articulate with an artificial socket. Alternatively, the intramedullary implant 10 may be used in connection with a modular proximal body and/or a modular neck to provide the upper stem portion 14, such that the shaft 12 and upper stem portion 14 are provided as a multi-piece configuration to allow independent sizing if desired.

Figure 3:
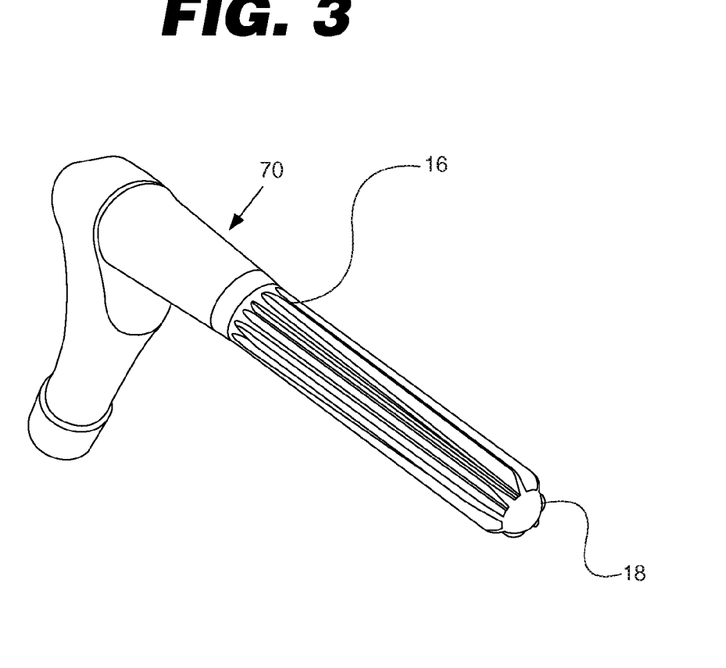
FIG. 3 is a side perspective view of the stem.

As best seen in FIG. 3, the shaft 12 has a proximal end 16 and a distal end 18. The distal end 18 is adapted to be inserted into a patient's intramedullary canal to secure the stem in place. The distal end 18 may be flat, rounded, bullet-nosed (as shown), or any other useful configuration.

Figure 4:
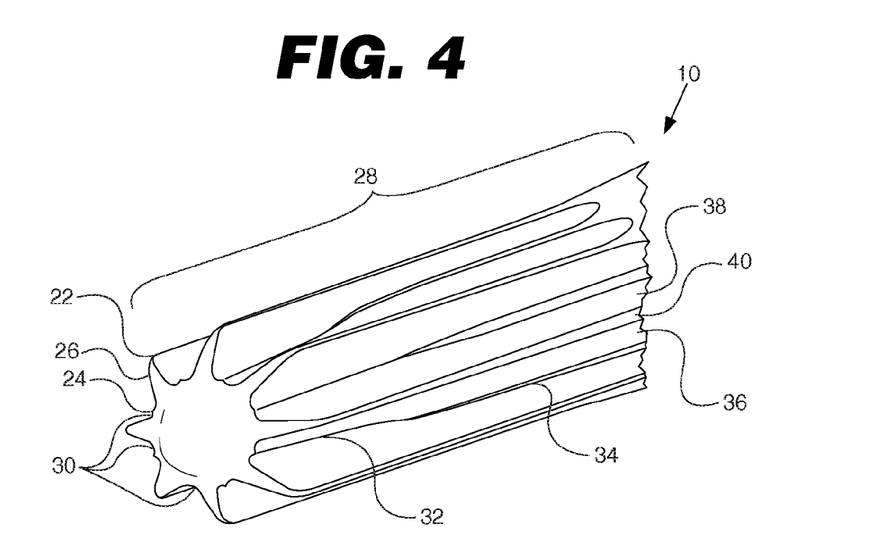
FIG. 4 is a detailed perspective view of a distal portion of the stem.

The length of shaft 12 is shown having a series of flutes 20. The series of flutes 20 is provided, among other things, for rotational and axial stability. FIG. 4 shows certain flutes on the intramedullary implant 10 that are formed in a triangular cross-sectional shape, with each flute having an apex 22, a base 24, and tapering sides 26. This formation will be referred to as being cross-sectionally tapered because of the configuration of tapering sides 26. Although an apex is typically thought of as a point where two sides meet, the flute apexes described herein need not be a point; it may be rounded, square, or any other shape. The term is simply being used to refer to the outermost portion of the flute. Although not shown, it is also possible for flutes to have parallel (or substantially parallel) sides rather than tapered sides. This formation will be referred to as substantially parallel-sided flutes. Cross-sectionally-tapered flutes add extra support against stem subsidence but substantially parallel-sided flutes or a combination of substantially parallel sided and cross-sectionally tapered flutes may also be used. The flutes also may provide support against rotation. It is also possible for a single flute to have both cross-sectional taper and parallel-sided features at different points along its length.

Another type of tapering that the series of flutes 20 may have is a narrowing apex. A narrowing apex may be featured on a cross-sectionally tapered flute or a parallel-sided flute. A flute with a narrowing apex may have a base 24 that maintains a similar size throughout the length of the flute but an apex 22 that narrows as the flute extends longitudinally and that preferably narrows from the proximal end to the distal end of the stem. This narrowing may be a smooth narrow (i.e., a traditional taper), or it may be a stepped narrowing like sawtooth or a series of ledges having substantially straight sides.

Figure 2:
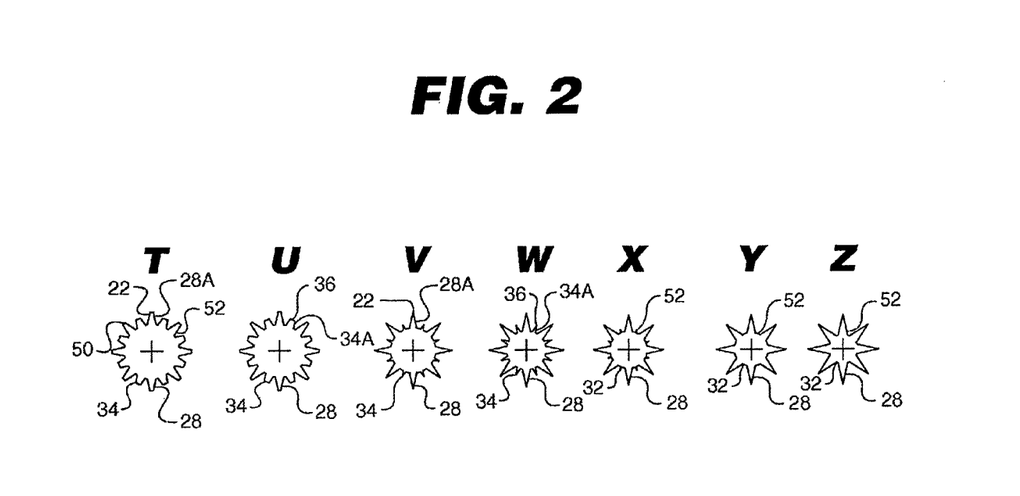
FIG. 2 illustrates various cross sections of the stem of FIG. 1 that correspond by letter to cross sections indicated on FIG. 1.

For example, the flute 28A shown in FIG. 2 appears to have a relatively flat apex 22 in cross section T. The apex narrows to a tapered point in cross sections V-Z. If provided, the narrowed apex preferably narrows as the flute extends longitudinally distally (as shown in FIG. 4), although, if desired, the apex may narrow as the flute extends proximally instead.

In certain embodiments, flutes having the described configurations may extend the substantial length of the shaft 12 or any part of shaft, and will be referred to as primary flutes 28. The apexes 22 of primary flutes 28 (whether or not they are provided as narrowing apexes) define an outer profile 50 of stem shaft, as shown in FIG. 2. Outer profile 50 may have a substantially constant diameter along the shaft 12, it may taper as it extends longitudinally, or it may be oval, oblong, rectangular, or any other desired configuration. In the depicted embodiments, the outer profile 50 is cylindrical (or substantially cylindrical) and maintains a similar diameter throughout much of the length of the shaft 12, although the outer profile 50 may slightly decrease in size or taper longitudinally toward the distal end 18 of the stem.

The bases 24 of primary flutes 28 define an inner profile 52 (or core) of stem shaft 12. Inner profile 52, as opposed to the embodiment with an outer profile of relative constant diameter, preferably tapers as it extends longitudinally and distally as shown in FIG. 2, but this is not required and other profiles are possible. This tapered core 52 allows additional surface area of the flutes to be exposed, increasing the flutes' ability to "grab" into bone. In essence, the flutes 28 form ledges or wedges that may be used to grab the sides of the femoral canal for enhanced stability.

Figure 5:
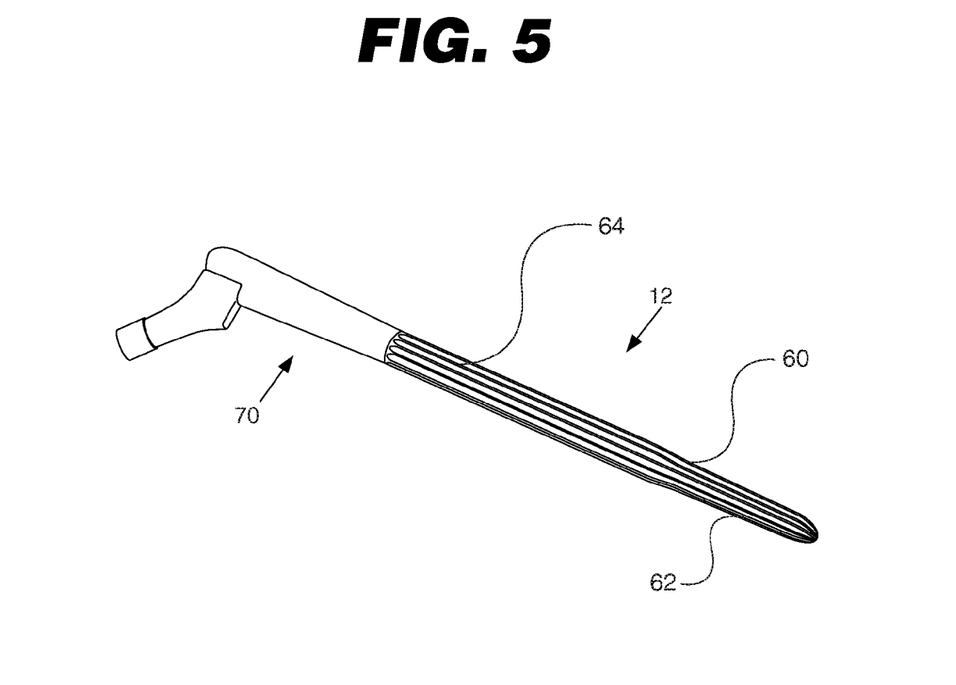
FIG. 5 is a side perspective view of a second embodiment of the stem.

Another type of flute that optionally may be provided on intramedullary implant 10 is secondary flute 34. Secondary flutes 34 may be provided in any of the above-described configurations, and they are preferably provided at a different level than primary flutes 28. For example, as shown in FIGS. 3 and 5, secondary flutes 34 may have an apex 36 that is shorter or less pronounced than primary flutes 28. This shortening may be a stepped down-type configuration (e.g., an angled sawtooth profile), or the flutes may taper in the longitudinal direction as they extend down the stem. Alternatively, the flutes may maintain a constant shape throughout their length. Preferably, secondary flutes taper longitudinally as they extend distally down shaft, as shown in the cross-sections of FIG. 2. Preferably, they also have a narrowed apex 36 (similar to the narrowed apex embodiment for primary flutes 28) as shown by the secondary flute 34A in cross sections U and W. In cross section U, the apex is relatively blunt and in cross section W, the apex has narrowed to more closely resembled a point or some other narrowed portion.

Additionally, as with primary flutes, secondary flutes 34 may be cross-sectionally tapered or substantially parallel-sided. They may extend the substantial length of shaft or any part of shaft.

FIG. 4 shows one embodiment of a potential configuration of secondary flutes 34. In this figure, the bases 24 of two primary flutes 28 may meet to form a valley 30. In certain embodiments, a valley 30 at the distal end 18 of shaft may be V-shaped, U-shaped, rounded, curved, or any other desired valley shape where the bases 24 of tapering sides 26 (or substantially parallel sides) of the primary flutes 28 meet. In other embodiments, a valley 30 at the distal end 18 of shaft may have a slight ridge 32, as shown in FIG. 4. Slight ridge 32 is the very tip of what may be a secondary flute 34. Secondary flutes 34 may begin at the proximal end 16 of shaft, along with primary flutes 28, and although they may be similar in size and shape to primary flutes 28, they are preferably provided a different level than primary flutes 28, and even more preferably, they are at least slightly smaller than primary flutes 28. They may have an apex 36, a base 38, and tapering sides 40. This formation will be referred to as being cross-sectionally tapered, because of the configuration of tapering sides 40. Although not shown, it is also possible for secondary flutes 34 to have parallel (or substantially parallel) sides rather than tapered sides. That formation will be referred to as substantially parallel-sided flutes. As with primary flutes, cross-sectionally-tapered secondary flutes also add extra support against stem subsidence, but parallel (or substantially parallel) sided flutes or a combination of substantially parallel sided and cross-sectionally tapered flutes may also be used. The flutes may also provide support against rotation. It is also possible for a single flute to have both cross-sectional taper and parallel-sided features at different points along its length.

In certain embodiments, secondary flutes 34 extend toward distal end 18 as they begin to taper out longitudinally (which will be referred to as a longitudinal taper). In other words, the apex 36 of the secondary flute 34 is smaller (meaning that its height can be shorter in relation to the core) at the apex at the distal end 18 than it is at the proximal end 16. In another embodiment, the term smaller may be used to refer to a smaller narrowed apex, if provided. This can be seen by the illustration at FIG. 2, which shows various cross sections of the shaft of FIG. 1 and how the core 52 tapers as the stem extends distally. In addition to showing the secondary flutes 34 longitudinally tapering, FIG. 4 also shows the narrowing apex feature.

Cross section T of FIG. 2 shows primary flutes 28 and secondary flutes 34 toward the proximal end 16 of shaft 12. The flutes are similar in shape and size, although primary flutes 28 appear to be slightly more pronounced or larger than secondary flutes 34. This is, again, a design consideration that those of ordinary skill in the art would understand can be manipulated based on the ultimate design needs.

Extending distally down shaft 12, cross section U shows that secondary flutes 34 begin to taper longitudinally. Cross sections V and W show further distal longitudinal tapering of the secondary flutes 34, in addition to a narrowing apex. Cross sections X-Z show that secondary flutes 34 eventually taper down to a sight ridge 32, and in some embodiments, secondary flutes 34 may taper out completely. In this or in other embodiments, the primary flutes 28 may form an outer profile 50 that is substantially constant at cross sections T, U, and V such that outer profile is a substantially cylindrical. If desired, outer profile 50 may begin to slightly taper as it extends longitudinally and distally, e.g., at cross section W, there may be the beginning of a longitudinal taper. There is also no requirement that stem 10 have a length long enough to support each of cross sections T-Z. It is possible to form a shorter stem that ends at, for example, cross-section W, if desired. Longer stems are also possible.

FIG. 2 shows an exemplary embodiment of a longitudinal tapering scheme, but it should be understood that any form of tapering, whether more pronounced and drastic or more gentle and slight, is considered within the scope of this invention.

Although various embodiments have been described and any combination of primary flutes 28, secondary flutes 34, outer profiles and inner profiles are possible and considered within the scope of this invention, a particularly preferred embodiment of the invention features cross-sectionally tapered primary flutes that form an outer profile 50 that remains substantially contrast throughout the length of the stem (at least until it reaches the distal portion 18 of the stem), a longitudinally tapered core 52 that tapers as it extends toward the distal end 18 of the stem, and cross-sectionally tapered secondary flutes 34 that longitudinally taper as they extend toward the distal end 18 of the stem.

One or more of the flutes on stem 10 may be provided with a bone in-growth or on-growth feature. This may be a roughened surface, metallic beads, a grit blasted surface, a porous surface, a hydroxyapatite or any other bone growth-promoting substance coating, combinations of any of these features, and so forth. This allows the bone into which the stem is implanted to integrate with the stem 10 or otherwise grow into the flutes 20 for increased strength and stability.

Providing a longitudinally tapered core 52 on stem 10 offers a number of advantages. Without being bound to any theory, one advantage may be that there is increased surface area for stabilization and bone on-growth or in-growth. This tapering also provides a relative flexibility to the stem that mimics the slight flexibility of bone. A tapered core also allows more area for the flutes to engage with bone, more fully securing the stem into place and making the most advantage of strong distal bone.

Providing longitudinally tapering secondary flutes 34 (or in other embodiments, stepped down secondary flutes 34) on stem 10 also offers a number of advantages. While not wishing to be bound to any theory, it is believed that one advantage of tapered secondary flutes 34 is that they provide additional surface area on the stem 10 for bone on-growth. Another advantage may be that the distal longitudinal tapering of secondary flutes 34 provides a wedge-like surface (i.e., at the narrowing apex the tapering flute) that can grab the sides of the intramedullary canal for enhanced stability. One potentially useful analogy may be to compare the resulting wedge-shaped apex surface of secondary flute 34 to a wedge-shaped door stop that can be lodged underneath a door to support it in a particular position. As the secondary flutes 34 engage with bone when the stem 10 is being inserted, the flutes cut and compress the bone, securing the stem in place. Various embodiments of the stem 10 may be used with or without bone cement. The primary flutes 28 also provide this stabilization function.

Another optional feature is that in lieu of the traditional bowing or distal anterior chamfering found in some longer stems, the shaft 12 may have a transitional region 60 that leads to a downsized section 62, as shown in FIG. 5. In this embodiment, the transitional region 60 separates a portion of the shaft having a first profile 64 and a portion of the shaft having a different, smaller profile (which in this case, is the downsized region 62). The transition region 60 may have an outer profile that is substantially cylindrical (and just smaller than the first profile 64) or it may have an outer profile with a taper. Any other profile geometry could be used as is considered within the scope of this invention, for example parabolic, trumpet-shaped, bell-shaped, a stepped or sawtooth configuration, one or more ledges (that may be any angle, such as, for example, 90 degree transition or angled ledge), and so forth. The first profile area 64 is preferably substantially cylindrical. This feature may be provided with or without the above-described flutes.

Figure 6:
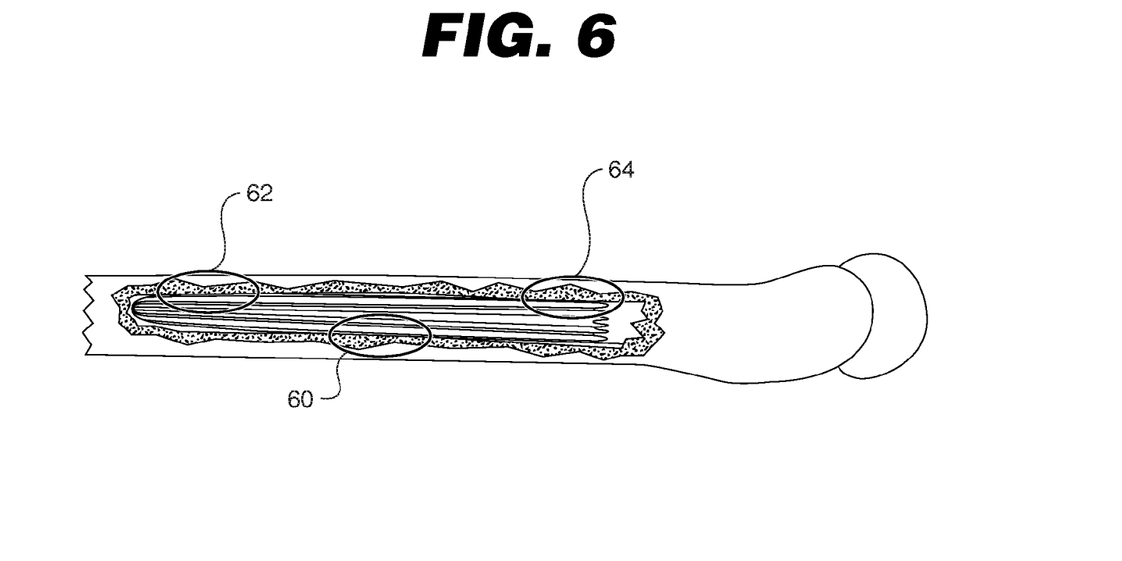
FIG. 6 is a side plan view of fixation points of the stem shown in FIG. 5.

The transitional region 60, if there is one, may be tapered, parabolic, stepped, or any other geometry, including those described above. Due to the transitional and downsized distal geometry, the fit obtained inside the intramedullary canal will be stable three-point fixation, as shown by the circled regions in FIG. 6. Using the transitional region 60 and the downsized cylindrical section 62 geometry to fit around the natural bow of the patient's femur provides the surgeon with near-infinite options for stem and neck fit. The transitional region 60 may also provide additional axial stability depending on the reaming procedure.

If desired, the transitional region/downsized cylindrical stem design configuration could also be used with a traditional-style bowed stem. Typically, a surgeon will over-ream (by 1 mm, for example, over the profile of the stem) when using a bowed stem prosthesis to mitigate the potential of a femoral fracture upon stem insertion. By downsizing the stem in the distal bowed region, the surgeon's technique is simplified because the stem is undersized in the critical region of the bow. Over-reaming is not necessary, as the surgeon can ream to the same profile as the proximal portion of the stem to achieve greater fixation proximally while facilitating insertion of the long bowed stem.

An alternate transition region 60 embodiment may be provided on a shaft with a first profile 64 but where the transition region 60 itself forms the remainder of the shaft. In other words, a separate downsized region 62 is not required. In this embodiment, the transition region 60 is preferably a tapered section.

In further embodiments, the stem flexibility may be enhanced by adding other distal features, such as slots, in one direction or multiple directions. A multi-directional slot may collapse and create a self-forming tapered section. Depending on reaming technique, these slots can be used for enhanced axial stability. The slot embodiment may be used in conjunction with the fluted stem design, the transitional stem design, or both.

Intramedullary implant 10 may be manufactured by producing a tapered core stem and maintaining a cylindrical outer profile via the flutes 20. The resulting flutes can be parallel sided or tapered. The resulting flutes may be provided in any number and shape. The flutes may be of consistent height or may differ in height or level such that the stem has secondary or tertiary flutes (or even more options) of various heights for different engagement levels. The flutes may also vary in length and/or width.

In one particular embodiment, there are eight primary flutes 28 and eight secondary flutes 34. There may be more or fewer numbers of each type of flute. The outer profile 50 (or contact surface) of the stem 10 can be cylindrical or any other relatively constant multi-sided shape, such as rectangular, oval, an oblong cross sectional shape, or any other shape that will provide the desired stability.

The stem may be made from any biocompatible material that has sufficient strength to withstand the patient's weight, examples of which include titanium, titanium alloys, stainless steel, stainless steel alloys, and other surgical grade material.

While the tapered core may be used in connection with the intramedullary implant 10, the location at which the taper begins along the stem length can be modified to provide additional axial support and any other desired characteristics.

Figure 7:
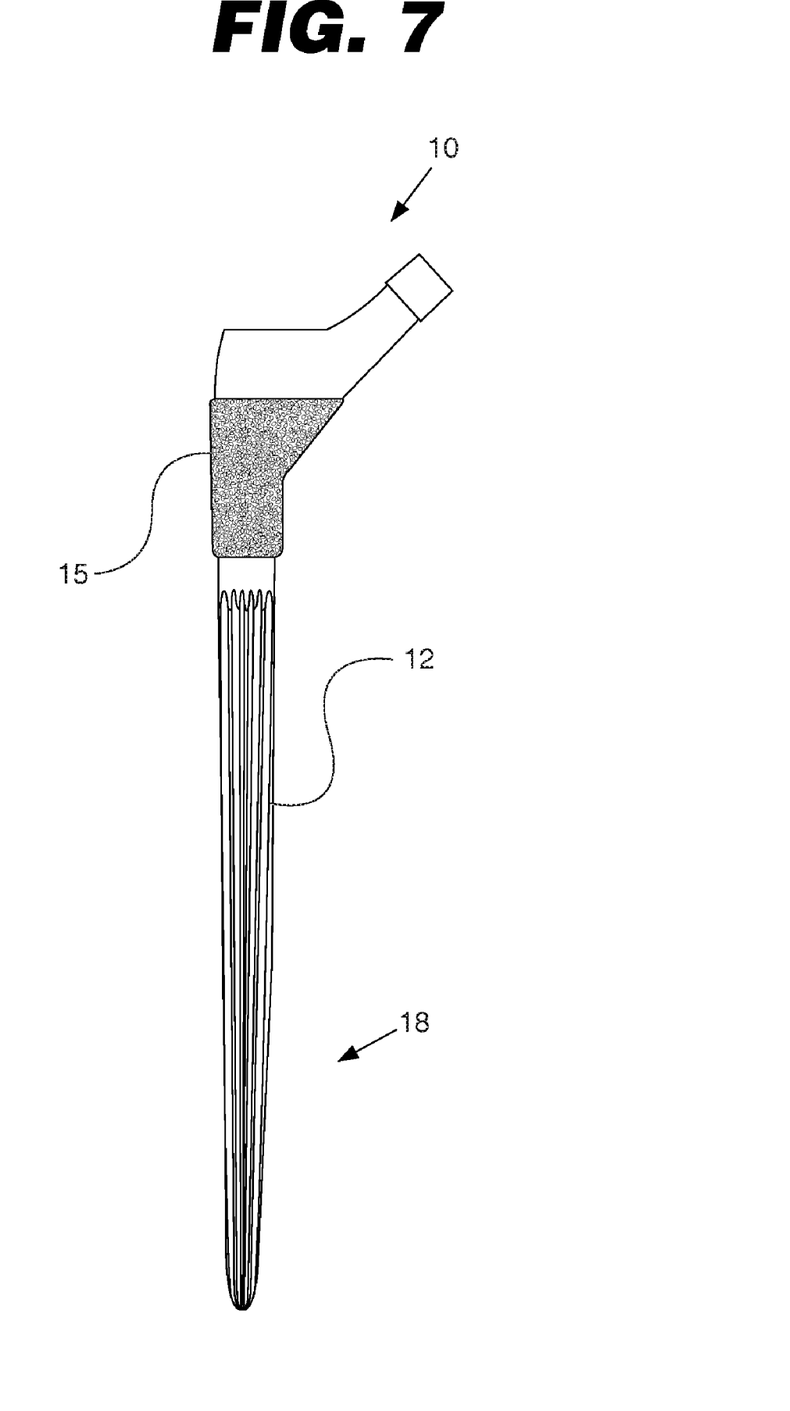
FIG. 7 is a side view of one embodiment of a modular stem with a sleeve body.

If provided, a modular body may be provided in the form of a sleeve 15 that slides over the distal end 18 of shaft 12, as shown in FIG. 7. Sleeve 15 may be any number of sizes to provide the surgeon with a greater degree of flexible options during the surgery. Although the sleeve 15 may have a substantially smooth surface, it also may be grit-blasted or have another kind of surface treatment. It is also possible for the sleeve 15 to have longitudinal grooves for reduced stiffness to more effectively load the femur. The grooves may be any shape or configuration. In certain embodiments, the grooves are formed using any of the design concepts described herein, such as primary flutes, secondary flutes, wedges, ridges, cross-sectionally tapered flutes, substantially parallel-sided flutes, longitudinally tapering flutes, or narrowing apex flutes.

FIGS. 8-19 illustrate alternative embodiments of the modular sleeve body 15. In these embodiments, the modular sleeve body has an inner portion, an outer portion, and one or more longitudinally extending bone engagement members. The bone engagement member is adapted for engaging bone and for placement of the modular sleeve body and the upper stem portion. The inner portion covers a segment of the upper stem portion, and the bone engagement member extends above or is raised relative to the outer portion. In some embodiments, the bone engagement member has a generally constant height relative to the outer portion. In other embodiments, the bone engagement member tapers in height relative to the outer portion. In some embodiments, the modular sleeve body may also include one or more grooves. The bone engagement member may incorporate features of the flutes and grooves described above. The outer portion and the bone engagement member may be of substantially the same material or different materials. In some cases, the bone engagement member may be made of a bioabsorbable material.

As best seen in FIGS. 1, 3, and 5, the upper stem portion 14 has a tapered member 70. The inner portion of the modular sleeve body is shaped to receive the tapered member 70. Thus, the modular sleeve body is adapted to connect to the upper stem portion. However, those having ordinary skill in the art would understand that the tapered member 70 could equally be located on the lower stem portion such that the modular sleeve body may be connected to the lower stem portion in some embodiments.

Figure 8:
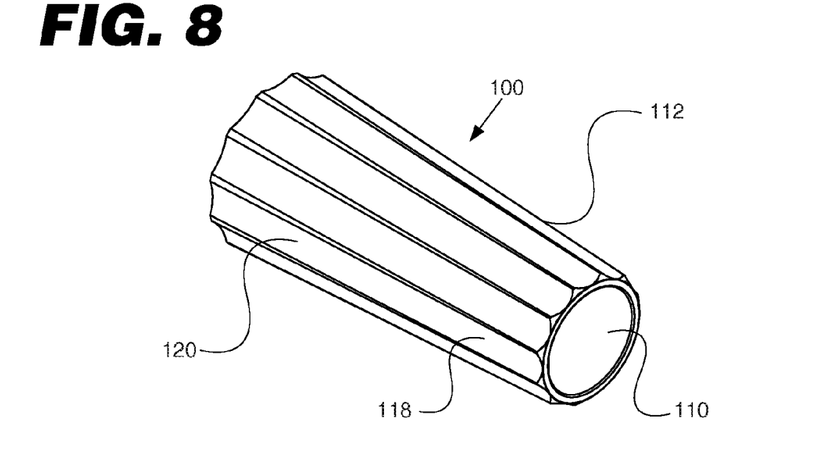
FIG. 8 is a front perspective view of a first alternative embodiment of the sleeve body.

FIG. 8 is a front perspective view of a first alternative embodiment of the sleeve body 100. The sleeve body 100 has an inner portion 110 and an outer portion 120. The sleeve body also includes one or more bone engagement members 112. The outer portion 120 of the sleeve body 100 is frustoconical. The bone engagement member 112 is tapered cross-sectionally along its length. In other words, the bone engagement member 112 increases in width while moving along its length. The sleeve body 100 includes one or more base portions 118. The base portion 118 is the area where the bone engagement member 112 extends to meet the outer portion 120. In the embodiment depicted in FIG. 8, the adjacent base portions 118 and the outer portion 120 form a substantially arcuate valley, or groove, between the peaks of the adjacent bone engagement members 112. The groove formed by the base portion 118 may be filled with, or used to hold, a medicament, bone cement, or other material before and/or during installation of the sleeve body 100 into bone.

Figure 9:
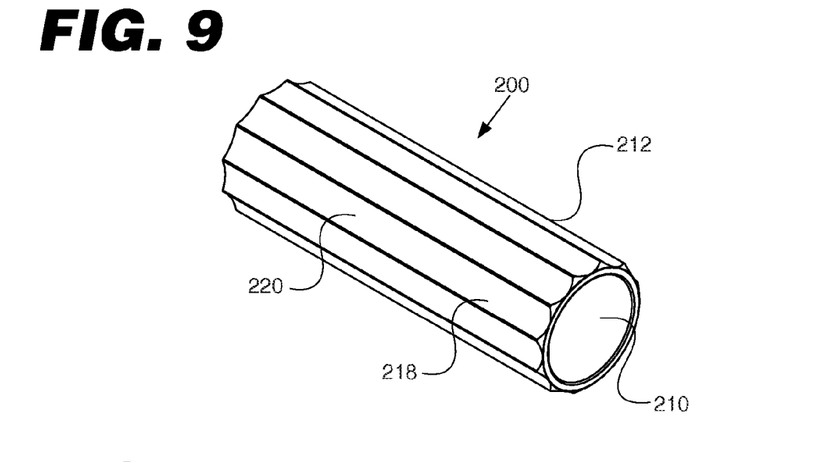
FIG. 9 is a front perspective view of a second alternative embodiment of the sleeve body.

FIG. 9 is a front perspective view of a second alternative embodiment of the sleeve body. The sleeve body 200 has an inner portion 210 and an outer portion 220. The sleeve body 200 also includes one or more bone engagement members 212. The outer portion 220 of the sleeve body 200 is cylindrical. The bone engagement member 212 has a distinct peak that extends substantially the length of the sleeve body 200. The sleeve body 200 includes one or more base portions 218. The base portion 218 is the area where the bone engagement member 212 extends to meet the outer portion 220. In the embodiment depicted in FIG. 9, the adjacent base portions 218 and the outer portion 220 form a substantially arcuate valley, or groove, between the peaks of the adjacent bone engagement members 212.

Figure 10:
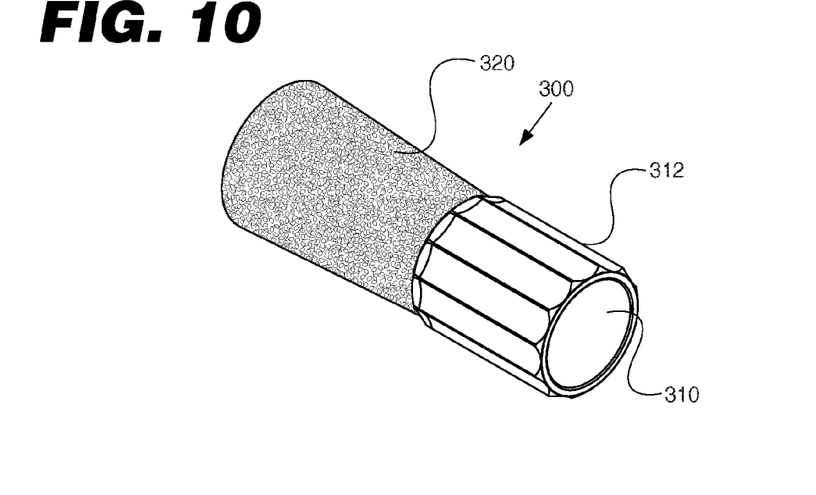
FIG. 10 is a front perspective view of a third alternative embodiment of the sleeve body.

FIG. 10 is a front perspective view of a third alternative embodiment of the sleeve body. The sleeve body 300 has an inner portion 310 and an outer portion 320. The sleeve body 300 also includes one or more bone engagement members 312. The outer portion 320 has a frustoconical region and a cylindrical region. In the embodiment depicted in FIG. 10, the bone engagement members 312 are located on the cylindrical region but equally could be on the frustoconical portion. In the embodiment depicted in FIG. 10, at least part of the outer portion 320 is textured but those having ordinary skill in the art would understand that the outer portion 320 may be completely textured. The textured surface may be formed by a sintered coating, a chemical etch, or through abrasive roughening.

Figure 11:
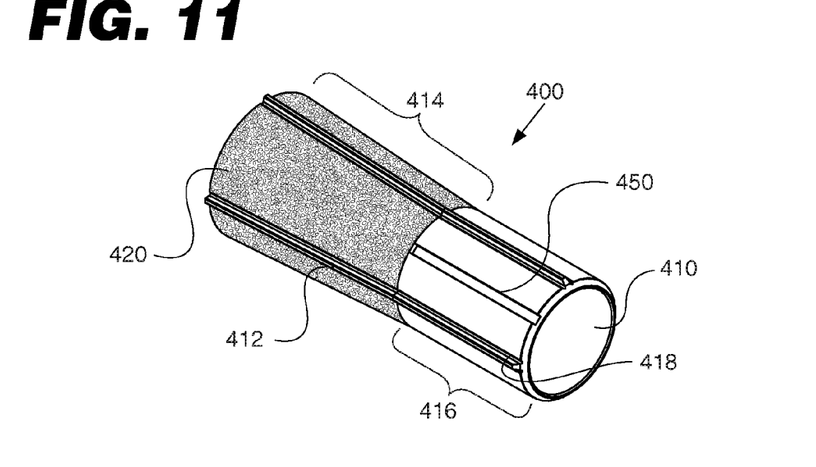
FIG. 11 is a front perspective view of a fourth alternative embodiment of the sleeve body.

FIG. 11 is a front perspective view of a fourth alternative embodiment of the sleeve body. The sleeve body 400 has an inner portion 410 and an outer portion 420. In the embodiment depicted in FIG. 11, part of the outer portion 420 is textured. The sleeve body 400 also includes one or more bone engagement members 412. The bone engagement member 412 has generally planar top portion. In other words, the bone engagement member 412 does not have a sharp peak. The sleeve body 400 has a proximal end portion 414 and a distal end portion 416. In the embodiment depicted in FIG. 11, at least one of the bone engagement members is located on the distal end portion 416. The sleeve body 400 may include one or more grooves 450. The groove 450 may be filled with, or used to hold, a medicament, bone cement, or other material before and/or during installation of the sleeve body 400 into bone. In the embodiment depicted in FIG. 11, the groove 450 is located on the distal end portion 416 but could equally be located on the proximal end portion 414. The sleeve body 400 includes one or more base portions 418. The base portion 418 is the portion of the sleeve body where the bone engagement member 412 meets the outer portion 420. In the embodiment depicted in FIG. 11, the base portion 418 is generally tapered.

Figure 12:
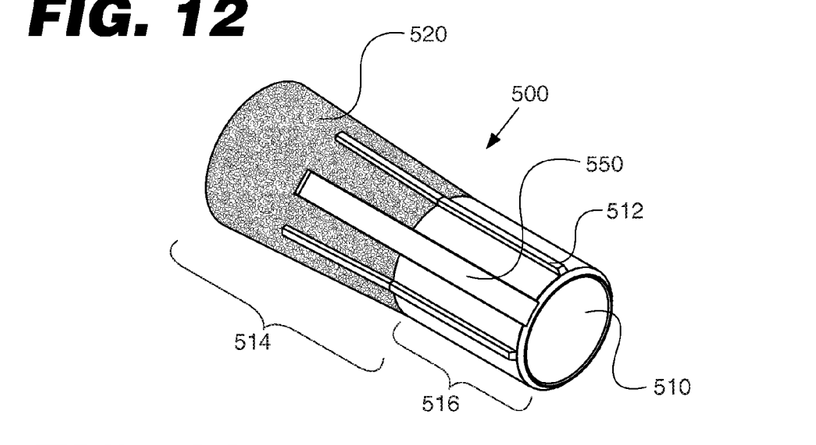
FIG. 12 is a front perspective view of a fifth alternative embodiment of the sleeve body.

FIG. 12 is a front perspective view of a fifth alternative embodiment of the sleeve body. The sleeve body 500 has an inner portion 510 and an outer portion 520. The sleeve body 500 also includes one or more bone engagement members 512. The sleeve body 500 has a proximal end portion 514 and a distal end portion 516. In the embodiment depicted in FIG. 12, at least one of the bone engagement members traverses both the proximal end portion 514 and the distal end portion 516. The sleeve body 500 may include one or more grooves 550. In the embodiment depicted in FIG. 12, the groove 550 traverses both the distal end portion 516 and the proximal end portion 514. The groove 550 may be filled with, or used to hold, a medicament, bone cement, or other material before and/or during installation of the sleeve body 500 into bone.

As best seen in FIGS. 11 and 12, the grooves 450, 550 may be any number of various widths. The width of the groove 450, 550 may be related to the width of the bone engagement member 412, 512. For example, the groove 450 depicted in FIG. 11 is approximately the same width as the bone engagement member 412, whereas the groove 550 is approximately three times the width of the bone engagement member 512. Those of ordinary skill in the art would understand, however, that the width of the groove may or may not be related to the width of the bone engagement member.

Figure 13:
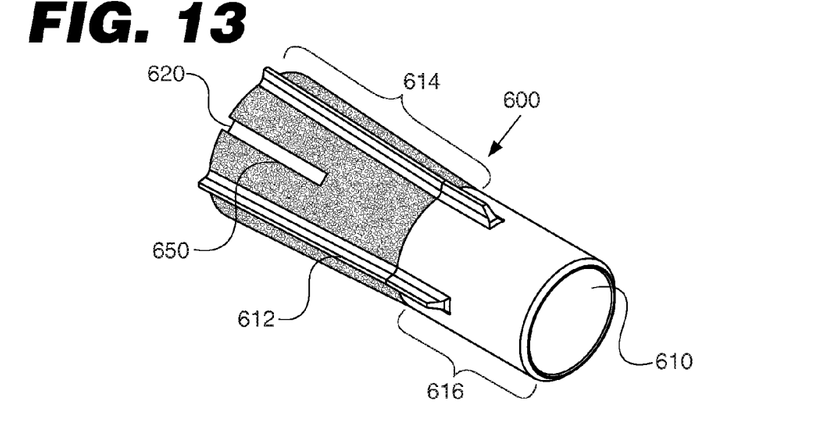
FIG. 13 is a front perspective view of a sixth alternative embodiment of the sleeve body.

FIG. 13 is a front perspective view of a sixth alternative embodiment of the sleeve body. The sleeve body 600 has an inner portion 610 and an outer portion 620. The sleeve body 600 also includes one or more bone engagement members 612. The sleeve body 600 has a proximal end portion 614 and a distal end portion 616. In the embodiment depicted in FIG. 13, at least one of the bone engagement members is located on the proximal end portion 614. The sleeve body 600 may include one or more grooves 650. In the embodiment depicted in FIG. 13, the groove 650 is located on the proximal end portion 614 but could equally be located on the distal end portion 616.

Figure 14:
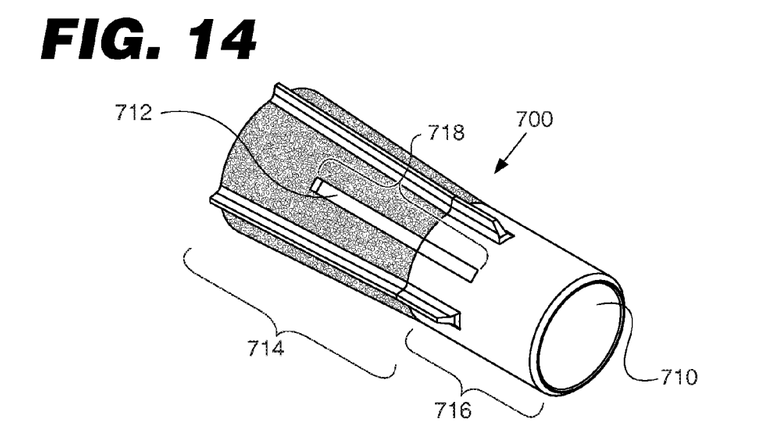
FIG. 14 is a front perspective view of a seventh alternative embodiment of the sleeve body.

FIG. 14 is a front perspective view of a seventh alternative embodiment of the sleeve body. The sleeve body 700 has an inner portion 710 and an outer portion 720. The sleeve body 700 also includes one or more bone engagement members 712. The sleeve body 700 has a proximal end portion 714, a distal end portion 716, and a middle portion 718. In the embodiment depicted in FIG. 14, at least one of the bone engagement members is located on the middle portion 718.

Figure 15:
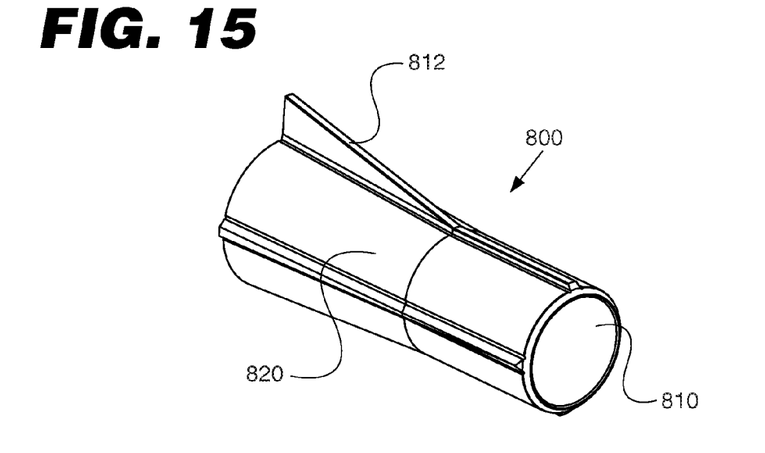
FIG. 15 is a front perspective view of an eighth alternative embodiment of the sleeve body.

FIG. 15 is a front perspective view of an eighth alternative embodiment of the sleeve body. The sleeve body 800 has an inner portion 810 and an outer portion 820. The sleeve body 800 also includes one or more bone engagement members 812. In the embodiment depicted in FIG. 15, the sleeve body 800 has four bone engagement members 812. The bone engagement member 812 tapers in height relative to the outer portion 820.

Figure 16:
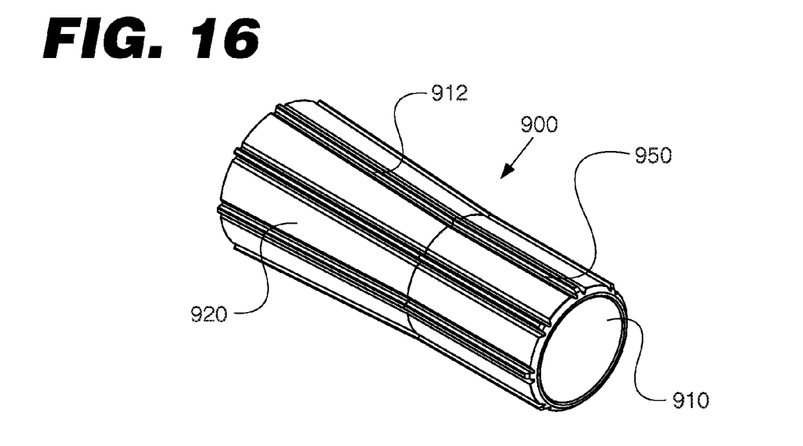
FIG. 16 is a front perspective view of a ninth alternative embodiment of the sleeve body.

FIG. 16 is a front perspective view of a ninth alternative embodiment of the sleeve body. The sleeve body 900 has an inner portion 910 and an outer portion 920. The sleeve body 900 also includes one or more bone engagement members 912. The sleeve body 900 may include one or more grooves 950. In the embodiment depicted in FIG. 16, the groove 950 is located generally adjacent the bone engagement member 912. In some embodiments, there is one groove 950 located on each side of the bone engagement member.

In some embodiments, the outer portion 920 is made of a first material and the bone engagement member 912 is made from a second material. For example, one of the materials may be a biocompatible metal whereas the other material is bioabsorbable. As used herein, the term "biodegradable" is used interchangeably with the terms "bioabsorbable", "bioresorbable", "resorbable", "degradable", "erodible", or "bioerodible", and these terms are used to characterize materials that are gradually replaced by bone after implantation into a human or an animal. In other instances, the outer portion 920 and the bone engagement member 912 may be made from substantially the same material.

Upon installation of the implant, gradual resorption of the bone engagement member or the sleeve body takes place. The biodegradable portions of the sleeve body or bone engagement member are at least partially manufactured of biodegradable materials, including, but not limited to, materials of a polymeric nature, or polymers. Biodegradable materials are biocompatible, meaning not eliciting unresolved inflammatory response or demonstrating extreme immunogenicity or cytotoxicity, by an intact material, any of its unreacted components, or degradation products. Further, biodegradable materials possess desirable combination of mechanical properties, such as those beneficial for providing proper support in the early stages of healing, and including, but not limited to, desirable compression, tension and torsion, characteristics. In general, the resorbable material is chosen such that it possesses a combination of desirable mechanical properties that are simultaneously advantageous for easy installation and for adequate fixation of the implant for a sufficient period of time necessary for healing and bone regrowth to occur. Advantageous mechanical properties include a sufficient amount of rigidity to prevent movement of the implant in the bone, and pliability to permit conformation of the implant to all or a portion of the unique shape of the cavity, thereby maximizing contact between the resorbable spacer, the implant and the bone.

Biodegradable materials are beneficial for promotion of tissue formation, with properties such as an amount of void space and degradation chosen to encourage tissue growth and vascularization, if appropriate, within the material. Degradation rate may be coupled to the rate of bone tissue formation so that neither the load-bearing capabilities of the tissue, nor tissue regeneration are compromised. Accordingly, degradation rate of biodegradable materials and a devices manufactured thereof are such so that to ensure adequate time for growth of bone tissue into a void, space, or cavity between a bone and a joint implant. In one particular embodiment of the present invention, a device is at least partially resorbed over a predetermined period of time, less than approximately several years, preferably less than approximately two years. The predetermined period of time is chosen depending on a particular application and can be, for example, less than approximately one year, or less than approximately three months, or less than approximately twelve weeks, or from approximately three to approximately eight weeks. As with all implanted materials, biodegradable materials are sterilizable to prevent infection. Sterilization, however, does not substantially interfere with the bioactivity of the material or alter its chemical composition, and does not substantially affect its biocompatibility or degradation properties.

The resorbable materials include, but are not limited to, polymeric materials, such as poly-alpha-hydroxy acids, polylactide and polyglycolide, including their copolymers, poly-(D,L-lactide-co-glycolide- ) and polyglycolide-co-trimethylencarbonate; stereopolymers, such as poly-(L-lactide) or poly-L-lactic acid (PLA), poly-(L-CO-D,L-lactide) and poly-(D,L-lactide), polyglactin acid (PGA), a combination thereof (PLA/PGA) or any derivative, combination, composite, or variation thereof, poly-(D,L-lactide-co-glycolide) (PDLLA-co-PGA), poly-(L-lactide) (PLLA), poly-(L-lactide) (PLLA), polyglycolide-co-trimethylencarbonate, (PGA-co-TMC), poly-(L-CO-D,L-lactide), poly-(D,L-lactide), (PDLLA). The use of slow degrading and highly crystalline polymers, such as poly-(L-lactide) and poly(L-CO-D,L-lactide) stereocopolymers with a low D,L amount, amorphous polymers, such as poly-(L-CO-D,L-lactide) stereocopolymers with a high D,L amount and the purous poly-(D,L-lactide), or fast-degrading copolymers, such as poly-(D,L-lactide-co-glycolide) or polyglycolide-co-trimethylencarbonate, is envisioned and falls within the scope of the present invention. The use of injectable or crosslinkable polymers, including, but not limited to, photopolymerizable and chemically polymerizable polymers and polymers that harden in situ, is also encompassed by the present invention, including but not limited to the use of polymers of sebacic acid (SA), alone, or copolymers of SA and 1,3-bis (p-carboxyphenoxy) propane (CPP), or 1,6-bis (p-carboxyphenoxy) hexane (CPH), or poly(propylene fumarate) (PPF). Resorbable materials for use in the devices according to the embodiments of the present invention are not limited to the foregoing and includes any fully or partially degradable or erodible in a body chemical composition or material suitable for use in the devices according to the embodiments of the present invention, including but not limited to carbohydrates and derivatives thereof, such as such as cellulose or hyaluronic acid, in resorbable devices of the embodiments of the present invention. Modifications of polymeric materials to adjust their structural, mechanical or chemical properties, or facilitate biological responses in tissues is envisioned and falls within the scope of the present invention.

Figure 17:
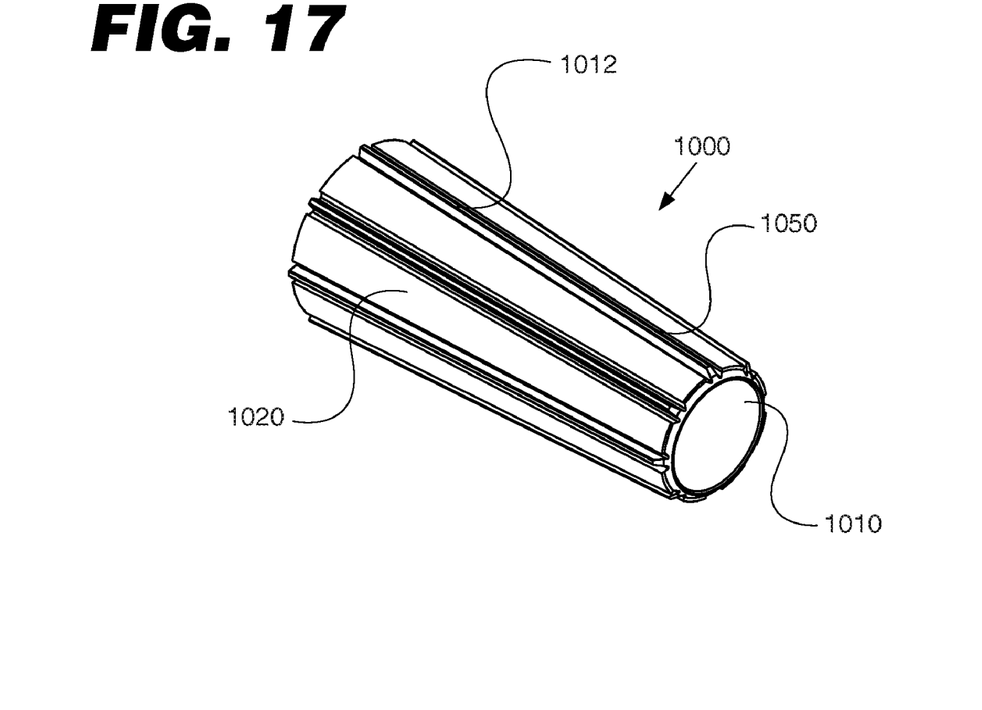
FIG. 17 is a front perspective view of a tenth alternative embodiment of the sleeve body.

FIG. 17 is a front perspective view of a tenth alternative embodiment of the sleeve body. The sleeve body 1000 has an inner portion 1010 and an outer portion 1020. In the embodiment depicted in FIG. 17, the inner portion 1010 and the outer portion 1020 are generally frusto-conical. The sleeve body 1000 also includes one or more bone engagement members 1012 and one or more grooves 1050.

Figure 18:
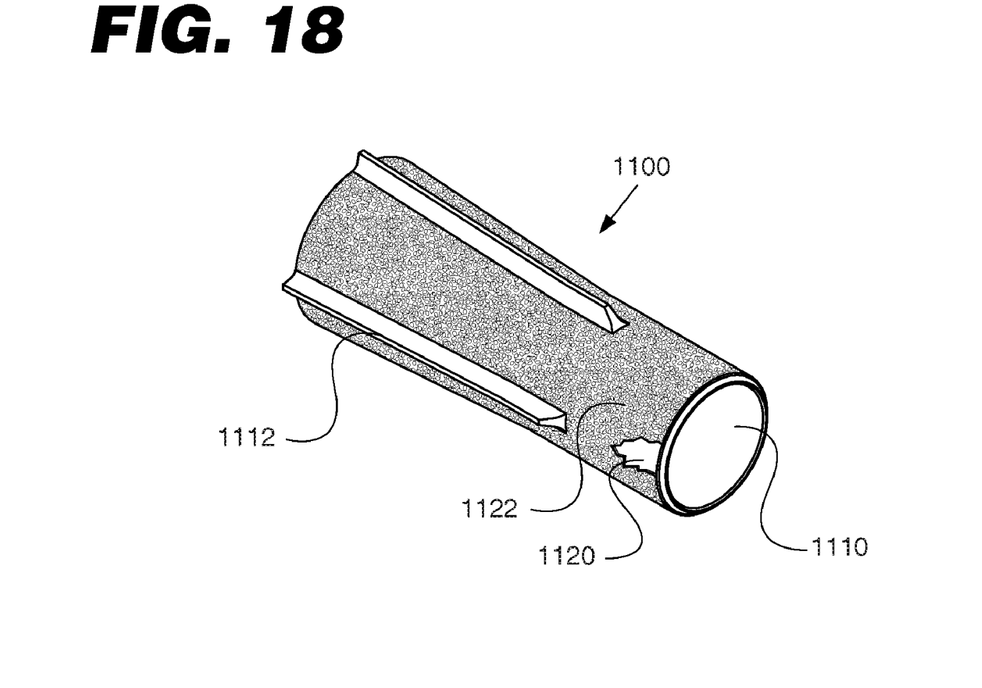
FIG. 18 is a front perspective view of an eleventh alternative embodiment of the sleeve body.

FIG. 18 is a front perspective view of an eleventh alternative embodiment of the sleeve body. The sleeve body 1100 has an inner portion 1110 and an outer portion 1120. The sleeve body 1100 also includes one or more bone engagement members 1112. The sleeve body may also include a casing 1122. The casing 1122 may also be known as a laminate or a shell. The casing 1122 may be made of a biocompatible metal alloy, a polymer, a ceramic, a composite, or a bioresorbable material. In the embodiment depicted in FIG. 18, the bone engagement members 1112 protrude above the casing 1122. However, in other embodiments, the casing 1122 may encapsulate the bone engagement members.

Figure 19:
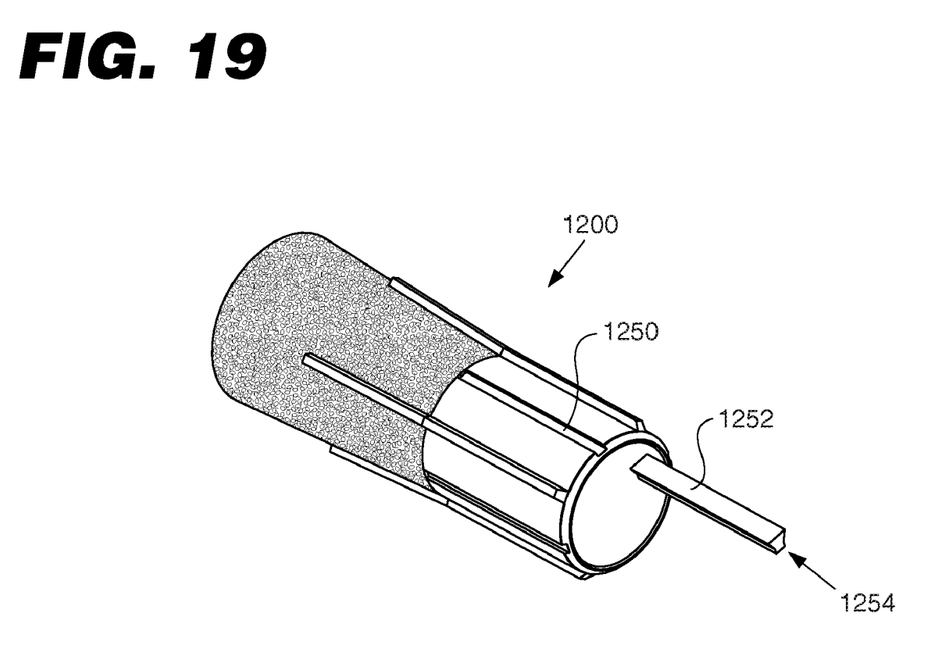
FIG. 19 is a front perspective view of a twelfth alternative embodiment of the sleeve body.

FIG. 19 is a front perspective view of a twelfth alternative embodiment of the sleeve body. The sleeve body 1200 may include one or more grooves 1250 and one or more auxiliary bone engagement members 1252. The auxiliary bone engagement member 1252 is modular such that bone engagement members 1252 may be added or removed from the sleeve body as required by the particular surgery. The auxiliary bone engagement member 1252 includes a connection member 1254. The groove 1250 and the connection member 1254 may have corresponding shapes for retention of the auxiliary bone engagement member 1252 to the sleeve body 1200. As examples, the groove 1250 and the connection member 1254 may have a sliding dovetail joint, a tapered-sided wedge joint, a straight-sided wedge joint, a radial slot with a spherical tongue, or a press fit.

Surgical Method

During a total hip replacement, the surgeon takes a number of measurements to ensure proper prosthesis selection, limb length and hip rotation. After making the incision, the surgeon gains access to the joint and pushes the femur out of the socket, exposing the joint cavity. The deteriorated femoral head is removed and the acetabulum is prepared by cleaning and enlarging with circular reamers of gradually increasing size. The new acetabular shell is implanted securely within the prepared hemispherical socket. The plastic inner portion of the implant is placed within the metal shell and fixed into place. If the surgery is a revision surgery, the previous implant will be removed and the bone prepared accordingly.

Next, the femur is prepared to receive the stem. The inside of the femoral canal is cleaned and enlarged by broaches, reamers, and other tools, creating a cavity that is smaller than, but that corresponds to the outer profile 50 of the implant stem 10. That outer geometry is dictated by the size and shape of the stem 10 and should be prepared so that the stem 10, upon insertion, will fit tightly and securely in the canal. The stem may be placed in the canal with or without cement. Typically, the flute geometry of the present invention would not be used with cement, although it would be possible. To supplement this joining, cables, bolts, grips, or struts could be used, examples of which are described in Application Publication Nos. 2004/0097942 and 2004/0087954. If a modular body, neck, stem, or any combination thereof is to be used to provide the upper stem portion of the implant, the proper size is selected and attached. Finally, the ball is seated within the cup so the joint is properly aligned and the incision is closed.

It should be noted that stems according to various embodiments of the invention may be used in impaction or compaction grafting procedures, where the surgeon uses a bone graft or like substance to rebuild bone before implanting the stem. For the same reason that the flutes engage the patient's intramedullary canal and provide a stable construct, they will similarly engage a bone graft.

Upon implantation, the tapered core 52 provides enhanced flexibility over a traditional cylindrically-shaped stem (fluted or solid), which should minimize some clinical consequences of stiff-stems such as thigh pain and osteolysis. Once the bone begins to grow onto the inner tapered core 52, the stem 10 should behave similar to a traditional tapered stem, where the body weight is transferred onto the femur more efficiently by a compressive force component. Clinical studies have indicated that a grit-blasted titanium stem surface will promote bone on-growth within weeks of surgery. Most patients are able to bear weight on the operated leg within several days of surgery.

In summary, some of the major advantages of the fluted, tapered-core, cylindrical stem design embodiments described are the ease of implantation, stem flexibility, and effective loading stress distribution. Similar advantages will be found with the transitional region embodiment. Because the distal stem can be prepared with traditional cylindrical reamers and consistently seated longitudinally within the canal, the surgical technique should be easier for the surgeon and more reproducible than with traditional tapered-style stems. This stem design is more flexible than traditional cylindrical stems and should exhibit more favorable stress distribution to the bone, resulting in less stress-shielding and osteolysis.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. An intramedullary implant for mounting within an intramedullary canal of a bone, the intramedullary implant comprising:
   a. a stem having an upper stem portion and a shaft, the shaft having a longitudinal length, a proximal end, and a distal end;
   b. a series of flutes disposed on the length of the shaft, each of said flutes comprising an apex and a base, the flute apexes defining an outer profile of the shaft, the flute bases defining a core of the stem, wherein the core tapers toward the distal end of the stem, the flute bases further comprising valleys with slight ridges near the distal end, wherein the ridges increase in size to form wedges as the ridges extend proximally up the stem; and
   c. a sleeve body connected to said upper stem portion, and said sleeve body having at least one longitudinally extending bone engagement member.

2. An intramedullary implant according to claim 1, further comprising
   said sleeve body having a first longitudinal length and comprising an outer portion, an inner portion for receiving the stem, and said at least one bone engagement member extending longitudinally from the outer portion of the sleeve body along a second longitudinal length, wherein the second longitudinal length is substantially shorter than the first longitudinal length.

3. The intramedullary implant according to claim 2, wherein said at least one longitudinally extending bone engagement member is tapered cross-sectionally along the second longitudinal length.

4. The intramedullary implant according to claim 2, wherein said sleeve body has a proximal end portion, a distal end portion, and a middle portion therebetween, and said at least one longitudinally extending bone engagement member is positioned on at least one of said proximal end portion, said distal end portion, and said middle portion.

5. The intramedullary implant according to claim 2, wherein at least one of the stem or the sleeve body is coated with hydroxyapatite.

6. The intramedullary implant according to claim 2, further comprising at least one groove defined in the outer portion of the sleeve body.

7. The intramedullary implant according to claim 6, further comprising an auxiliary bone engagement member that engages said groove.

8. The intramedullary implant according to claim 6, further comprising a base portion, and wherein said groove is defined in the base portion.

9. The intramedullary implant according to claim 1, wherein the bone engagement member comprises at least two sides, and wherein the sleeve body further comprises a groove located on each side of the bone engagement member.

10. An intramedullary implant according to claim 1 further comprising said sleeve body having an outer portion, an inner portion for receiving the stem, and at least one longitudinally extending bone engagement member protruding from the outer portion of the sleeve body, wherein the outer portion comprises a generally cylindrical portion and a generally frustroconical portion.

11. The intramedullary implant according to claim 10, wherein said at least one longitudinally extending bone engagement member has a constant height relative to the outer portion.

12. The intramedullary implant according to claim 10, wherein said at least one longitudinally extending bone engagement member is tapered relative to the outer portion.

13. The intramedullary implant according to claim 10, wherein said sleeve body further comprises a base portion where the bone engagement member meets the outer portion of the sleeve body.

14. The intramedullary implant according to claim 13, wherein a shape of said base portion is selected from the group consisting of arcuate and tapered.

15. The intramedullary implant according to claim 10, wherein said outer portion of said sleeve body and said at least one bone engagement member are comprised of a first material.

16. The intramedullary implant according to claim 15, further comprising a casing of a second material encapsulating the outer portion, and wherein said first material is different than said second material.

17. The intramedullary implant according to claim 16, wherein said second material is bioabsorbable.

18. The intramedullary implant according to claim 10, wherein said outer portion of said sleeve body comprises a first material and said at least one bone engagement member comprises a second material, and wherein said first material is different than said second material.

19. The intramedullary implant according to claim 18, wherein said second material is bioabsorbable.

20. The intramedullary implant according to claim 18, further comprising a casing of a third material encapsulating the outer portion, and wherein said third material is different than at least one of said first material or said second material.

21. The intramedullary implant according to claim 20, wherein said third material is bioabsorbable.

22. The intramedullary implant according to claim 20, wherein the at least one longitudinally extending bone engagement member protrudes through the casing.

23. The intramedullary implant according to claim 10, wherein said outer portion further comprises a textured surface.

24. The intramedullary implant according to claim 23, wherein said textured surface is selected from the group consisting of a sintered coating, chemically etched, and abrasively roughened.

25. The intramedullary implant according to claim 1, the shaft further comprising a transitional region.

26. The intramedullary implant according to claim 25, wherein the transitional region is tapered, parabolic, or stepped.

27. An intramedullary implant according to claim 1 said sleeve body further comprising an outer portion, an inner portion for receiving the stem, and a second bone engagement member that extends longitudinally along the outer portion and outwardly from the outer portion of the sleeve body.

28. The intramedullary implant according to claim 27, wherein the inner portion of the sleeve body covers at least a portion of the upper stem portion when the stem is received in the inner portion of the sleeve body.

29. The intramedullary implant according to claim 28, wherein at least one bone engagement member is cross-sectionally tapered.

30. The intramedullary implant according to claim 27, wherein at least one bone engagement member comprises a width and a longitudinal length, and wherein the width changes along the longitudinal length.

31. The intramedullary implant according to claim 27, wherein at least one bone engagement member comprises a height and a longitudinal length, and wherein the height changes along the longitudinal length.

32. The intramedullary implant according to claim 1, wherein at least a portion of an outer surface of the sleeve body further comprises at least one of a roughened surface, a porous surface, metallic beads, a grit blasted surface, or a hydroxyapatite.

33. The intramedullary implant according to claim 1, wherein an outer portion of the sleeve body comprises a generally cylindrical portion and a generally frustroconical portion.

34. The intramedullary implant according to claim 1, wherein at least a portion of an outer portion of the sleeve body further comprises at least one of a roughened surface, a porous surface, metallic beads, a grit blasted surface, or a hydroxyapatite.

35. The intramedullary implant according to claim 1, wherein an outer portion of the sleeve body comprises a non-textured region and a textured region, and wherein the textured region is formed by at least one of sinter coating, chemical etching, or abrasive roughening.

36. The intramedullary implant according to claim 35, wherein the bone engagement member extends from at least a portion of the non-textured region of the sleeve body.

37. The intramedullary implant according to claim 35, wherein the bone engagement member extends from at least a portion of the textured region of the sleeve body.

* * * * *